United States Patent [19]

Cho et al.

[11] Patent Number: 4,908,309

[45] Date of Patent: Mar. 13, 1990

[54] METHOD OF DETECTING CYSTEINE PROTEASES

[75] Inventors: Kyujin Cho, Livermore; David W. Rasnick, Sunol, both of Calif.

[73] Assignee: Prototek, Inc., Dublin, Calif.

[21] Appl. No.: 94,145

[22] Filed: Sep. 8, 1987

Related U.S. Application Data

[62] Division of Ser. No. 838,531, Mar. 11, 1986, Pat. No. 4,771,123.

[51] Int. Cl.$^4$ ................................................ C12Q 1/38
[52] U.S. Cl. ...................................... 435/23; 435/810
[58] Field of Search ............................ 435/23, 24, 810

[56] References Cited

U.S. PATENT DOCUMENTS 4,569,907  2/1986  Weingarten et al. ................ 435/23

FOREIGN PATENT DOCUMENTS 113996   7/1984  European Pat. Off. .............. 435/23
2140423  11/1984 United Kingdom ................. 435/23

Primary Examiner—Esther M. Kepplinger
Attorney, Agent, or Firm—Stephen C. Macevicz

[57] ABSTRACT

Peptide thioneamides are provided as synthetic substrates for cysteine proteases. The compounds of the invention are peptides consisting of one or more blocked or unblocked amino acids wherein the terminal carboxy of the peptides are thionated and forms a thioneamide linkage with a fluorogenic or chromogenic leaving group. The alpha carbonyls of the remaining amino acids are thionated or unthionated. The invention includes methods and kits for using the peptide thioneamides.

9 Claims, No Drawings

METHOD OF DETECTING CYSTEINE PROTEASES

CROSS-REFERENCE TO RELATED PATENT

This is a divisional application of U.S. patent application Ser. No. 838,531, filed Mar. 11, 1986, now U.S. Pat. No. 4,771,123.

BACKGROUND OF THE INVENTION

This invention relates to synthetic substrates and their use for determining the activities of enzymes, and more specifically, to peptide thioneamides and their use for determining the activities of cysteine proteases.

The determination of specific enzymes in biological fluids, such as blood, tissue homogenates, urine, or the like, is very useful for the diagnosis of certain diseases, e.g. Evered et al., eds. *Protein Degradation in Health and Disease* (Exerpta Medica, Amsterdam, 1980). Synthetic substrates have been developed and utilized for such determinations, resulting in clinical assay procedures having a high degree of specificity, reliability, and sensitivity. Synthetic substrates have generally been amino acid or peptide derivatives acylated to aromatic amines, the latter becoming fluorimetrically or spectrophotometrically detectable after being cleaved from the amino acid or peptide, e.g. see Lorand, ed.,"Proteolytic Enzymes," *Methods in Enzymology*, Vol. 80 (Academic Press, New York, 1981). The number and ordering of amino acids in the peptide moiety determines the enzyme specificity of a substrate. Enzyme activity is measured by the amount of the aromatic amine moiety liberated upon hydrolysis of a substrate. Exemplary synthetic substrates are disclosed in U.S. Pat. No. 3,862,011 dated Jan. 21, 1975 to Smith, U.S. Pat. No. 4,294,923 dated Oct. 13, 1981 to Smith et al.; and U.S. Pat. No. 4,505,852 dated Mar. 19, 1985 to Rasnick.

Enzyme specificity is an important criterion for the use of synthetic substrates in evaluating proteolytic activities, particularly in the clinical setting. For example, the accuracy and reliability of diagnostic tests based on measuring protease activities would be increased significantly if synthetic substrates were available which allowed the measurement of a particular protease activity in a biological fluid containing a host of related proteases. That is, such tests would be significantly improved by the availability of synthetic substrates for particular enzymes having little or no cross reactivity with related enzymes present in the same biological fluid.

The serine proteases are perhaps the best understood class of enzymes in their catalytic mechanism, and a number of highly specific synthetic peptide substrates are available for their detection. Cysteine proteases, on the other hand, have not shared the same intensity of interest until recently. During the last decade considerable interest in cysteine proteases has arisen as evidence of their involvement in a number of pathological conditions has become more certain. Cathepsins B, H, and L have been linked to inflammation, e.g. Ostensen et al. *Clin. Exp. Immunol.*, Vol. 54, pgs. 397–404 (1983), and protein degradation, e.g. Sutherland et al., *Biochem. Biophys. Res. Comm.*, Vol. 110, pgs. 332–338 (1983); McDonald et al., *Anal. New York Acad. Sci.*, Vol. 380 pgs. 178–186 (1982); Quinn et al., *Biochem. J.*, Vol. 172, pgs. 301–309 (1978); and Ishura et al., *J. Biochem.*, Vol. 94, pgs. 311–314 (1983). Many tumor cells have been found to secrete a cathepsin B-like cysteine protease which enables the tumor cells to invade the extra cellular matrix and to metastasize to secondary sites, e.g. Sloane et al., *Cancer Metastasis Reviews* Vol. 3, pgs. 249–263 (1984). Unfortunately such studies are limited because currently available synthetic peptide substrates used to assay cysteine proteases are often hydrolyzed by serine proteases, making it difficult to assign the observed activities to cysteine proteases with confidence.

More specific and selective substrates are necessary to improve or create new diagnostic tests based on cysteine protease activities, and to study the specific functions of cysteine proteases in normal and pathological states.

SUMMARY OF THE INVENTION

Accordingly, it is an object of the present invention to provide synthetic substrates which are preferentially hydrolyzed by cysteine proteases.

Another object of the invention is to provide synthetic substrates which are readily hydrolyzed by cysteine proteases, but to which serine proteases show little or no hydrolytic activity.

A further object of the invention is to provide peptide thioneamides as selective substrates for cysteine proteases in biological fluids.

Another object of the invention is to provide a method and kit for assaying the presence of cysteine proteases.

To achieve the foregoing objects, peptide thioneamides are provided as selective synthetic substrates for cysteine proteases. Generally the compounds of the invention are peptides consisting of one or more blocked or unblocked amino acids wherein the terminal carboxy of the peptides are thionated and forms a thioneamide linkage with a fluorogenic or chromogenic leaving group. The alpha carbonyls of the remaining amino acids are thionated or unthionated.

DETAILED DESCRIPTION OF THE INVENTION

The compounds of the invention are broadly defined by the formula:

$(AA)_n-AA\psi[CS]-W$   Formula I wherein:
$(AA)_n$ is a blocked or unblocked, thionated or unthionated amino acid whenever n=1, and $(AA)_n$ is a peptide consisting of blocked or unblocked, thionated or unthionated amino acids whenever n is greater than one. As used herein the term "thionated or unthionated amino acid" is defined by the following formula:

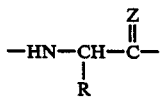

wherein R is defined by the particular amino acid employed, and Z is oxygen or sulfur. When the term "thionated" is used herein in reference to an amino acid Z is sulfur, and when the term "unthionated" is used Z is oxygen.

n is in the range of 0 to 12, and more preferably in the range of 0 to 4.

AAψ[CS] is a blocked or unblocked amino acid whose alpha carbonyl oxygen has been replaced with a sulfur atom (that is, the alpha carbonyl is a thiocarbonyl), and whose alpha amine forms a peptide bond with the alpha carbonyl of the adjacent amino acid of the $(AA)_n$ moiety whenever n is greater than or equal to one. AAψ[CS] is defined by the formula:

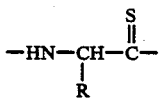

wherein R is defined by the particular amino acid employed.

W is a chromogenic or fluorogenic leaving group, such as 5-aminoisophthalic acid dimethylester (also referred to herein as AIE), 7-amino-4-trifluoromethylcoumarin (also referred to herein as AFC), 4-methoxy-2-naphthylamine (also referred to herein as MNA), 7-amino-4-methylcoumarin (also referred to herein as AMC), p-nitroaniline (also referred to herein as pNA), cresyl violet, rhodamine, or the like. Preferably W is a fluorogenic leaving group, such as AIE, AFC, MNA, AMC, pNA, or the like. Most preferably W is AIE.

The invention includes salts of the compounds defined by Formula I. In particular, such salts include hydrochloride, dihydrochloride, hydrobromide, dihydrobromide, trifluoroacetic, ditrifluoroacetic, and like salts.

The blocking groups which may be present on AAψ[CS] or on the amino acid or peptide represented by $(AA)_n$ are those well known in the art of peptide synthesis. For example, a listing of suitable peptide blocking groups is found in Gross et al., eds., *The Peptides*, Vol. 3 (Academic Press, New York, 1981). The particular choice of blocking group used in the compounds of the invention depends on several factors, including the blocking group's affect on enzyme specificity, its affect on substrate solubility, and its utility during synthesis. Suitable blocking groups include but are not limited to carbobenzoxy (Cbz), benzoyl, t-butoxycarbonyl (Boc), glutaryl, p-tolylsulfonyl (Tos), methoxysuccinyl (Meosuc), succinyl, glutaryl, and certain D-isomers of naturally occurring L-amino acids, including but not limited to D-proline, D-valine, and D-alanine.

Cysteine proteases detectable by compounds of the present invention include, but are not limited to, cathepsins B, H, L, N, S, T, I, J, and K, cancer procoagulant, papain, chymopapain, pyroglutamyl peptide hydrolase, calpain I and II, gamma-endorphin generating endopeptidase, viral cysteine protease, and the like. Selection of the most suitable substrate from the set defined by Formula I for detecting a given cysteine protease depends on the protease's specificity requirements. Generally, different cysteine proteases have different activities with respect to a given peptide bond, and the activities depend critically on the sequence of amino acids making up the peptide adjacent to the scissle bond. Consequently, picking the best compound of Formula I for detecting a particular cysteine protease may require some routine experimentation to determine the optimal peptide moiety for the protease. Preferably whenever the cysteine protease is cathepsin B the substrate is Cbz-Val-Lys-Lys-Argψ[CS]-W, Cbz-Arg-Argψ[CS]-W, Suc-Tyr-Metψ[CS]-W, beta-Ala-Tyr-Metψ[CS]-W, D-Leu-Tyr-Metψ[CS]-W, or Cbz-Ala-Arg-Argψ[CS]-W; whenever the cysteine protease is cathepsin L the substrate is Cbz-Phe-Argψ[CS]-W, Cbz-Arg-Argψ[CS]-W, Suc-Tyr-Metψ[CS]-W, Cbz-Ala-Arg-Argψ[CS]-W, beta-Ala-Tyr-Metψ[CS]-W, or D-Leu-Tyr-Metψ [CS]-W; whenever the cysteine protease is cathepsin H the substrate is Argψ[CS]-W, Cbz-Arg-Argψ[CS]-W, Suc-Tyr-Metψ[CS]-W, Cbz-Ala-Arg-Argψ[CS]-W, beta-Ala-Tyr-Metψ[CS]-W, or D-Leu-Tyr-Metψ[CS]-W; whenever the cysteine protease is pyroglutamyl peptide hydrolase the substrate is Pyro-Gluψ[CS]-W; whenever the cysteine protease is cathepsin E the substrate is Cbz-Gly-Gly-Argψ[CS]-W; whenever the cysteine protease is cathepsin M the substrate is Argψ[CS]-W; and whenever the cysteine protease is papain the substrate is Cbz-Lysψ[CS]-W, Meosuc-Phe-Thr(Obzl)ψ[CS]-W, or Cbz-Phe-Argψ[CS]-W. Here the conventional three letter designations for the amino acids have been used, e.g. "IUPAC-IUB Commission on Biochemical Nomenclature Symbols for Amino-Acid Derivatives and Peptides Recommendations (1971)," *J. Biol. Chem.*, Vol. 247, pgs. 977–983 (1972).

Generally compounds of the invention are synthesized by first forming an amino acid-leaving group conjugate, which may include suitable blocking groups. Next, the conjugate is thionated, preferably using Lawesson's, or like reagent, to form a thioneamide, e.g. see Cherkasov et al., "Organothiophosphorus Reagents in Organic Synthesis," *Tetrahedron*, Vol. 41, pgs. 2567–2624 (1985); Clausen et al., *Tetrahedron*, Vol. 37, p. 3637 (1981); and Yoe et al., *Tetrahedron*, Vol. 40, pgs. 2047–2052 (1984). Additional compounds of the invention are synthesized by linking a thionated or unthionated amino acid to the alpha amine of the thioneamide conjugate, and then to the alpha amine of the thionated or unthionated amino acid just attached, and so on, until a peptide thioneamide of desired length is obtained. The type of thionated amino acid linked to the leaving group, and the number and ordering of the thionated or unthionated amino acids added thereto in large part determine the enzyme specificity for the substrate. As indicated above, any combination of amino acids can be employed to obtain the desired specificity. In some cases it may be desirable to employ one or more thionated amino acids in the $(AA)_n$ moiety to prevent degradation of the substrate by serine proteases which may be present in a sample fluid. Such thionated peptides can be synthesized following the procedures disclosed in Thorsen et al., *Tetrahedron*, Vol. 39, pgs. 3429–3435 (1983); or in Clausen et al., *J. Chem. Soc. Perk Trans. I*, pgs. 785–798 (1984). Accordingly, both of these articles are incorporated by reference.

The method of the present invention for determining the presence of an enzyme in an enzyme-containing analyte comprises contacting the analyte with a substrate which can be hydrolyzed with an enzyme. Such analyte is usually a natural biological fluid, such as blood, serum, urine, tissue homogenate, or the like, but it can also be a synthetic solution used for quality control or as a reference standard. In any case the amount of substrate contacted with the sample fluid must be great enough so that a detectable fluorescent or colorimetric signal is generated for the reaction conditions employed. This amount of substrate is referred to herein as an effective amount.

The analyte-substrate mixture is incubated under enzyme hydrolyzing conditions. The pH of the mixture is generally in the range of the normal physiological environment of the enzyme, and thus can vary from one enzyme to another. The pH of the mixture is conveniently controlled by mixing the analyte and substrate in an appropriate buffering agent, such as N-tris(hydroxymethyl)methyl-2-aminoethane sulfonic acid (TES), or the like. In some cases, the concentration of certain divalent metal ions, such as $Ca^{++}$, $Mg^{++}$, or the like, must be regulated for proper enzyme action. The term "buffering agent" comprehends the inclusion of agents, e.g. EDTA, to effect such regulation when needed. The temperature at which the enzyme hydrolysis is effected is not critical, and may fall within a broad range, provided that the temperature is high enough to ensure enzyme activity, but not too high to cause degradation or other harmful reactions involving the substrate, enzyme, or other components of the mixture.

Fluorimetric or spectrophotometric determination of the liberated fluorophor or chromophor can be either a rate determination or and end point determination. Rate determinations are preferred because they are generally more sensitive and precise. In a rate determination, the fluorescence and/or absorption of the substrate-analyte mixture may be determined promptly after the analyte is contacted with the substrate. In an end point determination, enzyme hydrolysis is allowed to proceed for a predetermined length of time, e.g. for about 5 to 60 minutes, preferably for about 15–30 minutes. Such reaction time is selected so that a sufficient quantity of fluorophor and/or chromophor is released as to provide an acceptable degree of accuracy for the assay.

Standard fluorimeters or spectrophotometers are used to make the fluorescence intensity measurements and/or absorption measurements, e.g. see Pearson et al., *Clin. Chem.*, Vol. 27, pgs. 256–262 (1981); Udenfriend, *Fluorescence Assay in Biology and Medicine*, Vol. I and II (Academic Press, New York, 1961 and 1967); or U.S. Pat. No. 4,388,233, to name just a few references describing appropriate fluorimetric or colorimetric detection apparatus.

Substrates of the invention are useful for a variety of analytical techniques. They can be utilized in biological studies to determine the presence of cysteine proteases in single cells or tissues, and they are useful to determine the presence of cysteine proteases in biological fluids of clinical importance. The substrates can be used as indicators in connection with various chromatographic or electrophoretic techniques. The appropriate substrate can be applied to the chromatographic or electrophoretic medium to indicate the location and/or density of a previously separated enzyme. Finally, the substrates of the invention can be used to classify enzymes as cysteine proteases or not.

The following examples serve to illustrate the present invention. The concentrations of reagents, choice of temperatures, choice of solvents, and values of other variable parameters are only to exemplify the practice of the present invention and are not to be considered as limitations thereof.

EXAMPLE I

Synthesis of Cbz-Argψ[CS](Mtr)-AIE

Mtr-Cl and Cbz-Arg(Mtr)-OH were synthesized by the method of Fujino et al., *Chem. Pharm. Bull.*, Vol. 29, pgs. 2825–2831 (1981). Here "Mtr" refers to 4-methoxy- 2,3,6-trimethylbenzenesulfonyl, which is employed as a blocking group for the guanidino moiety of arginine. Mixed anhydride coupling method was employed to obtain Cbz-Arg(Mtr)-AIE ($R_f^1$ 0.57). Cbz-Arg(Mtr)-OH (5.00 g, 9.62 mmol) was dissolved in 50 ml of tetrahydrofuran (THF) containing 1 eq N-methylmorpholine (NMM), and cooled to $-15°$ C. Isobutyl chloroformate (IBCF) was then added and the mixture stirred for 2.5 minutes, after which AIE (2.01 g, 9.62 mmol) dissolved in 20 ml of dimethylformamide (DMF) and cooled to $-15°$ C., was added. The mixture was stirred in an ice-methanol bath and slowly warmed to room temperature overnight. The next day, the mixture was evaporated to an oil which was taken up in EtOAC, and washed twice with 10% citric acid, once with $H_2O$, twice with saturated $NaHCO_3$, and once with brine. The organic layer was dried over $MgSzo_4$ and the solvent evaporated. The residue was dissolved in 100 ml $CH_2Cl_2$ and precipitated in ether. The product was filtered, dried under reduced pressure over $P_2O_5$ and NaOH to give a 47% yield. The material showed a single spot on tlc with $R_f^1$ 0.57.

10 equivalents of Lawesson's reagent (2,4-bis-(4-methoxyphenyl)-2,4-dithiooxo-1,3,2,4-dithiadiphosphetan available from Fluka) (2.8 g, 7.0 mmol) was added to Cbz-Arg(Mtr)-AIE dissolved in 10 ml of benzene, and the mixture was refluxed for 10 hrs. The reaction was followed by the appearance of a slightly higher $R_f^1$ material on tlc. At the completion of thionation, excess Lawesson's reagent was filtered off, solvent evaporated, and the product purified on a silica gel column. The byproduct of Lawesson's reagent was eluted with 100% $CHCl_3$, and then the desired product was eluted with 1% methanol/$CHCl_3$. After evaporation to a small volume the desired product was precipitated in ether, filtered, and dried under reduced pressure over $P_2O_5$ and NaOH. Tlc showed a single spot with $R_f^1$ 0.61. (The corresponding oxyamide showed $R_f^1$ 0.57). Yield: 39%.

EXAMPLE II

Synthesis of Argψ[CS]-AIE.2HBr

Removal of both Cbz and Mtr from Cbz-Arg[CS](Mtr)-AIE was accomplished simultaneously by treatment with 31% HBr/Acetic acid for 3 hrs. at room temperature. The product was precipitated in ether and purified on a Sephadex LH-20 column with 100% methanol as eluent.

EXAMPLE III

Synthesis of Cbz-Lys(Boc)ψ[CS]-AIE

Cbz-Lys(Boc)-AIE was obtained by the mixed anhydride coupling method as described above for Cbz-Arg(Mtr)-AIE. Here "Boc" refers to t-butoxycarbonyl, which is employed as a blocking group for the epsilon amine of lysine. Cbz-Lys(Boc)-AIE (1 g, 1.75 mmol) was refluxed in 10 ml benzene with 5 equivalents (1.77 g, 4.38 mmol) of Lawesson's reagent for 10 hrs. Upon completion of the thionation, the same workup was followed as with Cbz-Argψ[CS](Mtr)-AIE, except that the product was eluted with 0.5% methanol/CHC13 from a silica gel column. The homogeneous material showed an $R_f^1$ 0.89. (The corresponding oxyamide: $R_f^1$ 0.83)

EXAMPLE IV

Synthesis of Cbz-Lysψ[CS]-AIE.HCl

Cbz-Lys(Boc)ψ[CS]-AIE was dissolved in $CH_2Cl_2$ and was treated with an equal volume of saturated HCl/dioxane at 0° C. for 1 hr. The product was then precipitated in ether, filtered, and dried under reduced pressure over $P_2O_5$ and NaOH. Tlc showed a single spot with $R_f$ 0.56. (The corresponding oxyamide: $R_f$ 0.48).

EXAMPLE V

Synthesis of Cbz-Phe-Argψ[CS]-AIE.HBr

The trichlorophenyl ester of benzyloxycarbonylphenylalanine (Cbz-Phe-OTcp) (58.8 mg, 0.123 mmol, 1.5 eq) was combined with Argψ[CS]-AIE.2HBr (50.0 mg, 0.082 mmol) in 3 ml DMF. While stirring, N-methylmorpholine (NMM) (22.6 microliter, 0.205 mmol) and a catalytic amount of 1-hydroxybenzotriazole (HOBT) (1 mg) were added, and the solution was stirred overnight at room temperature. After evaporation of the solvent, the oily material was dissolved in a small amount of MeOH/CHCl$_3$ (1:9) and precipitated in ether. The product was then filtered and dried under reduced pressure to give a 94% yield. The material showed a single spot on tlc, $R_f$ 0.71 (the corresponding oxyamide: $R_f$ 0.64)

EXAMPLE VI

Synthesis of Cbz-Argψ[CS](Mtr)-AFC and Deprotected Hydrobromide Salt Thereof Synthesis proceeds as described in Example I, except that AFC is substituted for AIE to obtain Cbz-Arg(Mtr)-AFC, which is then used in the thionation step. The hydrobromide salt is obtained as described in Example II.

EXAMPLE VII

Synthesis of Cbz-Argψ[CS](Mtr)-AMC and Deprotected Hydrobromide Salt Thereof Synthesis proceeds as described in Example I, except that AMC is substituted for AIE to obtain Cbz-Arg(Mtr)-AMC, which is then used in the thionation step. The hydrobromide salt is obtained as described in Example II.

EXAMPLE VIII

Synthesis of Cbz-Lys(Boc)ψ[CS]-AFC and Deprotected Hydrochloride Salt Thereof Synthesis proceeds as described in Example III, except that AFC is substituted for AIE to obtain Cbz-Lys(Boc)-AFC, which is then used in the thionation step. The deprotected hydrochloride salt is obtained as described in Example IV.

EXAMPLE IX

Synthesis of Cbz-Lys(Boc)ψ[CS]-AMC and Deprotected Hydrochloride Salt Thereof Synthesis proceeds as described in Example III, except that AMC is substituted for AIE to obtain Cbz-Lys(Boc)-AMC, which is then used in the thionation step. The deprotected hydrochloride salt is obtained as described in Example IV.

EXAMPLE X

Catalysis of Oxyamides and Thioneamides by Trypsin and Papain.

Table I below provides a comparison between hydrolysis rates of trypsin and papain acting on two different oxyamides and on their corresponding thioneamides. Trypsin was used at pH 7.5 in a Tris buffer (50 mM), with 10 mM CaCl$_2$, and 12.5% DMSO. Papain was used at pH 6.5 in a thiol buffer (52 mM NaH$_2$PO$_4$, 31 mM dithiothreitol, 2.1 mM EDTA) and 12.5% DMSO.

Table I lists the catalytic constants $k_{cat}$ (moles product formed per second per mole enzyme), $K_M$ (M), and $k_{cat}/K_M$ (M$^{-1}$sec$^{-1}$) for the indicated substrates.

TABLE I

| Substrate | Trypsin | Papain |
|---|---|---|
| Cbz—Lys—AIE: | | |
| $k_{cat}$ | $1.15 \times 10^{-1}$ | $2.95 \times 10^{-2}$ |
| $K_M$ | $1.68 \times 10^{-4}$ | $2.81 \times 10^{-4}$ |
| $k_{cat}/K_M$ | $6.86 \times 10^2$ | $1.05 \times 10^2$ |
| Cbz—Lys ψ[CS]—AIE: | | |
| $k_{cat}$ | | $4.00 \times 10^{-3}$ |
| $K_M$ | NO RATE | $2.13 \times 10^{-4}$ |
| $k_{cat}/K_M$ | | $1.88 \times 10^1$ |
| Cbz—Phe—Arg—AIE: | | |
| $k_{cat}$ | $9.03 \times 10^{-1}$ | $3.53 \times 10^1$ |
| $K_M$ | $5.02 \times 10^{-4}$ | $8.13 \times 10^{-4}$ |
| $k_{cat}/K_M$ | $1.80 \times 10^3$ | $4.35 \times 10^4$ |
| Cbz—Phe—Arg ψ[CS]—AIE: | | |
| $k_{cat}$ | | 5.35 |
| $K_M$ | NO RATE | $5.74 \times 10^{-4}$ |
| $k_{cat}/K_M$ | | $9.32 \times 10^{-2}$ |

Trypsin, a serine protease, showed no measurable rates of product formation for either thioneamide. Papain, a cysteine protease, catalysed product formation for both oxyamides and thioneamides.

Table II below shows the selective detection of papain in the presence of trypsin using Cbz-Lysψ[CS]-AIE. A thiol buffer at pH 6.5 was used (52 mM NaH$_2$PO$_4$, 31 mM dithiothreitol, 2.1 mM EDTA) with 2.5% DMSO. The enzyme concentrations in the assays were $6.85 \times 10^{-6}$ M for papain, and $1.28 \times 10^{-6}$ M for trypsin. Substrate concentrations were $2.46 \times 10^{-4}$ M for Cbz-Lys-AIE, and $2.53 \times 10^{-4}$ M for Cbz-Lysψ[CS]-AIE. Rates are given in terms of moles AIE formed per minute.

TABLE II

| Enzyme | Cbz—Lys—AIE | Cbz—Lys ψ[CS]—AIE |
|---|---|---|
| Papain | 6.03 | 1.15 |
| Trypsin | 1.54 | 0.00 |
| Papain and Trypsin | 8.15 | 1.12 |

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A method of detecting cysteine proteases in a sample fluid, the method comprising the steps of:
   forming a mixture comprising a buffering agent, the sample fluid, and an amount effective as a substrate for cysteine proteases of a compound, or salt thereof, defined by the formula:

wherein:
   $(AA)_n$ is a blocked or unblocked, thionated or unthionated amino acid whenever $n=1$, and (AA)$_n$ is a peptide consisting of blocked or unblocked, thionated or unthionated amino acids whenever n is greater than one, n is in the range between 0 and 12 inclusive, AAψ[CS] is a blocked or unblocked amino acid whose alpha carbonyl oxygen has been replaced with a sulfur atom, and whose alpha amine forms a peptide bond with the alpha carbonyl of the adjacent amino acid of the (AA)$_n$ moiety whenever n is greater than or equal to one, and W is a chromogenic or fluorogenic leaving group covalently attached to the carbon atom of the alpha carbonyl of AAψ[CS]; and relating the change in color or fluorescence of the mixture to the activity of the cysteine protease as said compound is hydrolysed thereby.

2. The method of claim 1 wherein (AA)$_n$ is a blocked or unblocked, unthionated amino acid whenever n=1, and (AA)$_n$ is a peptide consisting of blocked or unblocked, unthionated amino acids whenever n is greater than one.

3. The method of claim 2 wherein n is in the range of 0 to 4 inclusive, and wherein W is a fluorogenic leaving group.

4. The method of claim 3 wherein W is selected from the group consisting of 5-aminoisophthalic acid dimethylester, 7-amino-4-trifluoromethylcoumarin, 4-methoxy- 2-naphthylamine, 7-amino-4-methylcoumarin, and p-nitroaniline.

5. The method of claim 4 wherein W is 5-minoisophthalic acid dimethylester.

6. A kit for detecting the presence of a cysteine protease in a sample fluid, the kit comprising:

a buffering agent; and an amount effective as a substrate for cysteine proteases of a compound, or salt thereof, defined by the formula:

(AA)$_n$—AAψ[CS]-W wherein:

(AA)$_n$ is a blocked or unblocked, thionated or unthionated amino acid whenever n=1, and (AA)$_n$ is a peptide consisting of blocked or unblocked, thionated or unthionated amino acids whenever n is greater than one;

n is in the range between 0 and 12 inclusive;

AAψ[CS] is a blocked or unblocked amino acid whose alpha carbonyl oxygen has been replaced by a sulfur atom, and whose alpha amine forms a peptide bond with the alpha carbonyl of the adjacent amino acid of the (AA)$_n$ moiety whenever n is greater than or equal to one; and W is a chromogenic or fluorogenic leaving group covalently attached to the carbon atom of the alpha carbonyl of AAψ[CS].

7. The kit of claim 6 wherein (AA)$_n$ is a blocked or unblocked, unthionated amino acid whenever n=1, and (AA)$_n$ is a peptide consisting of blocked or unblocked, unthionated amino acids whenever n is greater than one.

8. The kit of claim 7 wherein n is in the range of 0 to 4 inclusive, and wherein W is selected from the group consisting of 5-aminoisophthalic acid dimethylester, 7-amino-4-trifluoromethylcoumarin, 4-methoxy-2-naphthylamine, 7-amino-4-methylcoumarin, and p-nitroaniline.

9. The kit of claim 8 wherein W is 5-aminoisophthalic acid dimethylester.

* * * * *